United States Patent
Inman

[11] Patent Number: 5,158,774
[45] Date of Patent: Oct. 27, 1992

[54] METHOD OF TREATING YEAST INFECTION

[76] Inventor: Wanda V. Inman, 909 Connor Rd., Chester, S.C. 29706

[21] Appl. No.: 564,112

[22] Filed: Aug. 8, 1990

[51] Int. Cl.$^5$ .......................... A61K 31/05; A61K 9/08
[52] U.S. Cl. .................... 424/430; 424/195.1; 424/717; 514/724; 514/967
[58] Field of Search ...................... 424/430, 195.1, 71, 424/967, 466

[56] References Cited
U.S. PATENT DOCUMENTS
4,725,576  2/1988  Pollock et al. ...................... 424/54

Primary Examiner—Thurman K. Page
Assistant Examiner—Carlos Azpuru
Attorney, Agent, or Firm—Leon Gilden

[57] ABSTRACT

A method includes the step of providing an aqueous solution, including alcohol, thymol, and Eucalyptol for use as a douching solution, whereafter the solution is directed within a douching vessel, the vessel agitated, and a vaginal douching procedure performed.

1 Claim, No Drawings

METHOD OF TREATING YEAST INFECTION

BACKGROUND OF THE INVENTION

1. Field of the Invention

The field of invention relates to methods and solutions of treating vaginal fungal or yeast infections, and more particularly pertains to a new and improved method of treating yeast infections including an aqueous solution of alcohol, menthol, and methyl salicylate, Eucalyptol, and thymol.

2. Description of the Prior Art

Treatment of fungal infections are difficult, as such infections are particularly resistive to treatment with antibacterials and antibiotics. A class of dermatophytic infections of a somewhat different type is infections of the mucous membranes effected by trichomonal or monilial organisms. This type of vaginitis may be brought to bear by a variety of causes that expose the tissue to such infection of the monilial type. Prolonged use of tetracyclines, steroid therapy, diabetes and pregnancy are common causes. Typically, topical application to effect curing of such infections have been utilized to include p-tolyl diiodomethyl sulfone compound. This topical treatment of fungal or yeast infections on the skin of warm blooded animals to include individuals has been utilized in a relatively effective manner.

Such prior art may be found in U.S. Pat. No. 4,185,120 to Smith. A further treatment of fungal infections may be found in U.S. Pat. No. 4,790,989 to Hunter, et al. Topical sulfones utilized are found in U.S. Pat. No. 3,657,353 to Crovetti, et al. and to U.S. Pat. No. 3,632,859 to Crovetti. U.S. Pat. No. 3,663,623 to Crovetti sets forth a further iodomethylsulfones compound.

As such, it may be appreciated that there continues to be a need for a new and improved method of treating yeast fungal and infections by solution and in this respect, the present invention substantially fulfills this need.

SUMMARY OF THE INVENTION

In view of the foregoing disadvantages inherent in the known types of anti-fungal al creams and lotions now present in the prior art, the present invention provides a method of treating yeast infections wherein the same utilizes an aqueous solution and mixture to combat fungal infections. As such, the general purpose of the present invention, which will be described subsequently in greater detail, is to provide a new and improved method of treating yeast infections which has all the advantages of the prior art anti-fungal treatments and none of the disadvantages.

To attain this, the present invention provides a method including the step of providing an aqueous solution, including alcohol, thymol, and Eucalyptol for use as a douching solution, whereafter the solution is directed within a douching vessel, the vessel agitated, and a vaginal douching procedure performed.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved method of treating yeast infections which has all the advantages of the prior art anti-fungal treatments and none of the disadvantages.

It is another object of the present invention to provide a new and improved method of treating yeast infections which may be easily and efficiently manufactured and marketed.

It is a further object of the present invention to provide a new and improved method of treating yeast infections which is of a durable and reliable construction.

An even further object of the present invention is to provide a new and improved method of treating yeast infections which is susceptible of a low cost of manufacture with regard to both materials and labor, and which accordingly is then susceptible of low prices of sale to the consuming public, thereby making such methods of treating yeast infections economically available to the buying public.

Still yet another object of the present invention is to provide a new and improved method of treating yeast infections which provides in the apparatuses and methods of the prior art some of the advantages thereof, while simultaneously overcoming some of the disadvantages normally associated therewith.

Still another object of the present invention is to provide a new and improved method of treating yeast infections wherein the same utilizes a readily and easily administered douching solution to effectively combat vaginal fungal infection.

DESCRIPTION OF THE PREFERRED EMBODIMENT

A formulation of the anti-fungal solution set forth by the instant invention was made according to the following procedure:

The Listerine (TM) wherein an equivalent was prepared using a solution:

| | |
|---|---|
| Thymol | .06 Percent |
| Eucalyptol | .09 Percent |
| Methyl Salicylate | .06 percent |
| Menthol | .04 percent |
| Alcohol | 26.9 percent |

| | |
|---|---|
| Benzoic Acid | .01 percent |
| Water | 72.84 percent |

The Listerine (TM) or solution was mixed to provide an aqueous germicidal solution. Thereafter, the solution was directed into the 950 milliliters of water that was heated to a temperature defined between 99 degrees F. to 110 degrees F. Five milliliters of baking soda and 5 milliliters of salt were added to define the final solution that was agitated within the douching vessel, whereafter a douching procedure was effected with a female subject suffering from a diagnosed yeast or fungal infection. The procedure was subsequently repeated within twenty-four hours until the infection had cleared. Subsequent gynecological testing evidenced absence of infection.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly. all suitable modifications and equivalents may be resorted to, falling within the scope of the invention.

What is claimed as being new and desired to be protected by LETTERS PATENT of the United States is as follows:

1. A method of treating a vaginal fungal infection, comprising,
   a. Mixing an aqueous germicidal solution,
   b. Directing the solution into a douching vessel,
   c. Shaking the douching vessel for complete mixing of the solution,
   d. Effecting a vaginal douching procedure, and
   wherein the aqueous germicidal solution includes a first solution including thymol, Eucalyptol, methyl, Salicylate, menthol, water, and alcohol, and
   wherein the first solution is directed into a second solution including water, baking soda, and salt, and
   wherein the water of the second solution is initially elevated to a temperature between 99 and 110 degrees F.

* * * * *